United States Patent [19]

Tsukahara et al.

[11] Patent Number: 5,298,989
[45] Date of Patent: Mar. 29, 1994

[54] METHOD OF AND APPARATUS FOR MULTI-IMAGE INSPECTION OF BONDING WIRE

[75] Inventors: Hiroyuki Tsukahara, Atsugi; Yoshitaka Oshima, Isehara; Masato Nakashima, Yokohama, all of Japan

[73] Assignee: Fujitsu Limited, Kawasaki, Japan

[21] Appl. No.: 666,709

[22] Filed: Mar. 8, 1991

[30] Foreign Application Priority Data

Mar. 12, 1990 [JP] Japan ................................. 2-60852
Mar. 19, 1990 [JP] Japan ................................. 2-69237

[51] Int. Cl.⁵ .............................................. H04N 7/18
[52] U.S. Cl. ................................... 348/126; 356/237
[58] Field of Search ................. 358/106; 356/237; 359/381; 382/8

[56] References Cited

U.S. PATENT DOCUMENTS

| | | | |
|---|---|---|---|
| 4,305,096 | 12/1981 | Yokoshima et al. | 358/106 |
| 4,686,565 | 8/1987 | Ando | 358/106 |
| 4,816,686 | 3/1989 | Hara et al. | 358/106 |
| 4,872,052 | 10/1989 | Liudzius et al. | 358/106 |
| 5,023,917 | 6/1991 | Base | 358/106 |
| 5,135,303 | 8/1992 | Uto | 356/237 |

FOREIGN PATENT DOCUMENTS

| | | |
|---|---|---|
| 0374694 | 12/1989 | European Pat. Off. |
| 57-155743 | 9/1982 | Japan |
| 58-63144 | 4/1983 | Japan |
| 59-150433 | 8/1984 | Japan |
| 63-158847 | 7/1988 | Japan |
| 1-140048 | 6/1989 | Japan |

*Primary Examiner*—Alvin E. Oberley
*Assistant Examiner*—Minsun Oh
*Attorney, Agent, or Firm*—Staas & Halsey

[57] ABSTRACT

An optical system of inspecting bonding wires on a semiconductor by using a camera, focal length and depth adjusting unit, and an illumination device for irradiating brilliantly a desired portion of an inspection object with an illumination light. The focal length and depth adjusting means comprises a plurality of glass plates each having a different focal length and depth, and each bonding wire is inspected at a plurality of levels at a height position of the wire and at a plurality of portions thereof in its longitudinal direction to make a comparison between focal point evaluation quantities or feature quantities at each detected position so that wiring defects can be detected.

29 Claims, 14 Drawing Sheets

METHOD OF AND APPARATUS FOR MULTI-IMAGE INSPECTION OF BONDING WIRE

BACKGROUND OF THE INVENTION

This invention relates to a method of inspecting the outer form or appearance of a bonding wire bonded onto a semiconductor and an apparatus used for working of the method.

In recent years, according as semiconductor elements such as ICs, LSIs, COBs (chips on board), etc. have been highly integrated, and the quantity of productions has been increased, a method and an apparatus for carrying out inspection of the outer appearance of bonding wires connecting chips to package frames or boards in these semiconductor element highly integrated have been developed to find out wiring and ball defects such as broken or too close wires and incorrect wiring paths.

In such bonding wire inspection method and apparatus, it is required to inspect precisely the three-dimensional outer appearance of the bonding wires.

This kind of method and apparatus are disclosed in Japanese Patent Laid-Open Publication (Japanese Kokai) No. 139638/1984. In the conventional method and apparatus, there is provided a table movable horizontally and vertically for supporting a semiconductor as an inspection object. Over the table is disposed a camera which has a lens with a small focal depth and captures image of bonding wires on the semiconductor to send video signals to a signal processing unit.

The table for supporting the semiconductor is moved vertically little by little within the entire range of the semiconductor in its height direction. That is, the table is, firstly, stopped at a first position where the top portion of a bonding wire having a curved shape coincides with the focal point of the camera. At this time, an image at the top portion of the wire is displayed clearly or brightly with other portions thereof displayed dimly. Secondly, the table is moved slightly upwardly to stop at a second position where a portion of the wire slightly lower than the top portion thereof coincides with the focal point of the camera, resulting in that an image at a portion of the wire lower than the top portion thereof is displayed brightly with other portions thereof including its top portion displayed dimly. In this manner, the semiconductor as an inspection object is gradually moved to change the relative position between the focal point of the camera and the curved shape of the wire thereby to capture an image of portion of the wire which is located at position in focus. These images thus obtained are processed by the signal processing unit to recognize the three-dimensional shape of each bonding wire. Instead of the table, an optical system in the camera may be operated to change its focal point.

The above method and apparatus can be theoretically carried out and manufactured, respectively.

However, in this conventional method and apparatus, the table for supporting the semiconductor thereon or the optical system of the camera must be moved precisely intermittently to stop at a several of different positions within a small range corresponding to the height of the inspection object.

Therefore, the conventional method and apparatus is not fully satisfactory at present.

SUMMARY OF THE INVENTION

It is an object of the present invention to provide a method of and an apparatus for inspection of a bonding wire, which can effectively inspect the three dimensional shape of the bonding wire on a semiconductor to find out wiring and ball defects.

According to one aspect of this invention, there is provided a method of inspection of bonding wires on a semiconductor as an inspection object in which a camera captures an image of said inspection object while irradiating it with an illumination light to obtain a video signal which is to be processed to detect wiring defects, said method comprising the steps of: determining a plurality of combinations with respect to focal depth and length of said camera; capturing an image of at least one selected portion of a bonding wire with a combination of a certain focal length and a certain depth to obtain a feature portion thereof in a certain height of said wire, respectively; capturing an image at said portion of the bonding wire with a combination of another focal length different from said certain focal length and a certain depth to obtain a feature quantity on the basis of luminance distribution at said portion thereof in another height position of said wire, a similar image capture operation being repeated a predetermined number of times, with different focal length and depth in a different height position of said wire; and making a comparison between a plurality of feature quantities at said portion at different height positions of said wire to detect wiring defects.

According to another aspect of this invention, there is provided an apparatus for inspection of bonding wires on a semiconductor as an inspection object in which a camera captures an image of said inspection object while irradiating it with an illumination light to obtain a video signal which is to be processed to detect wiring defects, said apparatus comprising; focal length and depth adjusting means provided between said inspection object and said camera; feature quantity extraction means for extracting feature quantities of at least one selected point of said wire on the basis of luminance distribution at said point; and judgement means for making a comparison between said feature quantities at different height positions of said wire at said selected point thereof to detect wiring defects.

According to still another aspect of this invention there is provided an apparatus for inspection of bonding wires on a semiconductor as an inspection object in which a camera captures an image of said inspection object while irradiating it with an illumination light to obtain a video signal which is to be processed to detect wiring defects, said apparatus comprising, an illumination device for irradiating said inspection object with an illumination light, which has an annular illumination unit for emitting said illumination light in an annular shape, an optical path changing unit for directing said illumination light to said inspection object located in said optical changing unit, and a driving unit for moving vertically said optical changing unit.

Further objects, features and other aspects of this invention will be understood from the detailed description of the preferred embodiments of this invention with reference to the drawings.

BRIEF DESCRIPTION OF THE DRAWINGS

In the accompanying drawings:

FIG. 5(A) and (B) are a luminance distribution characteristic diagram wherein FIG. 5A is a luminance distribution diagram taken along the line A-B in FIG. 4 in the case of an in-focus state.

FIGS. 6(A) to (C) are an explanatory view for judging whether the form of the bonding wire is normal or defective, wherein FIG. 6A is a diagram showing a normal wire, FIG. 6B is a view showing a wire suspending defect, and FIG. 6C is a view showing a wire stretching defect;

FIG. 8(A) to (C) are a plan view showing an image of an inspection object when it is irradiated by respective illumination units, wherein FIG. 8A is a plan view of an image of inspection object when it is irradiated by an optical path changing unit, FIG. 8B is a plan view of an image of the inspection object when it is irradiated by a vertical illumination unit, and FIG. 8C is a plan view of an image of the inspection object when it is irradiated by a back illumination unit;

DETAILED DESCRIPTION OF THE INVENTION

Figure 1:
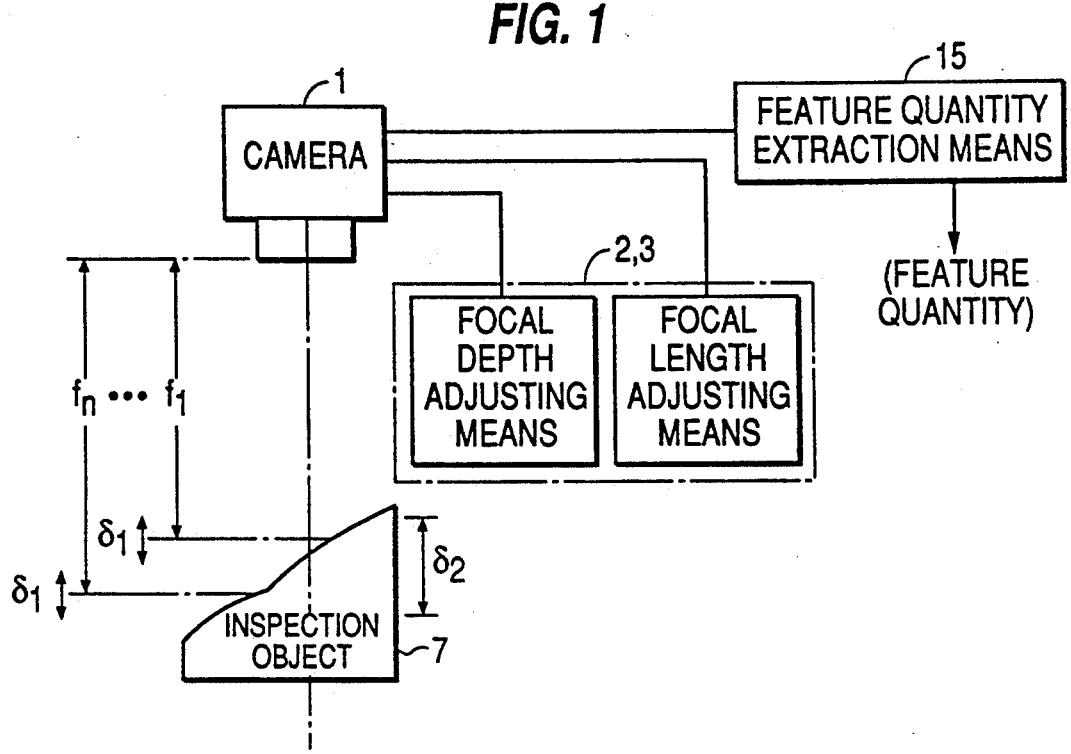
FIG. 1 is an explanatory view showing the principle of this invention.
Figure 2:
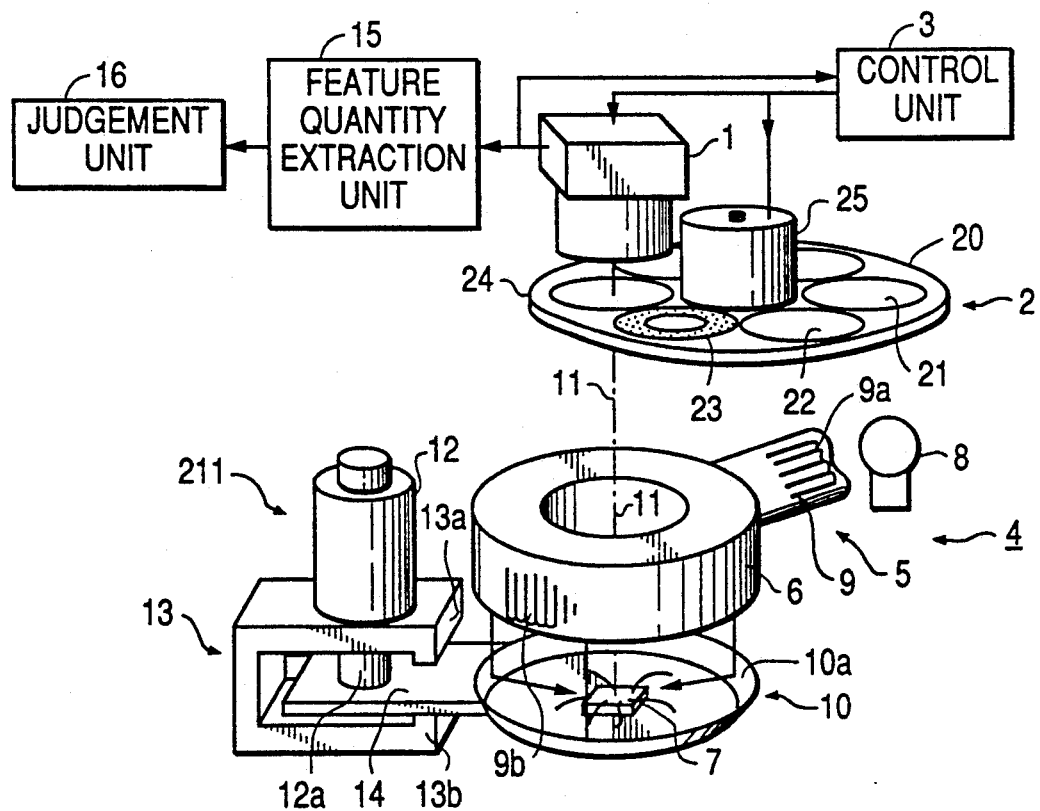
FIG. 2 is a diagrammatic view showing the structure of a bonding wire inspection apparatus according to this invention.

In FIGS. 1 and 2, a wire bonding inspection apparatus for inspecting of a bonding wire on a semiconductor is shown comprising a camera arranged oppositely to an inspection object 7 such as a semiconductor having a three dimensional structure to capture an image of the inspection object 7 and to output a video signal. An adjustment unit is provided between the camera and the inspection object 7 for adjusting the focal depth (depth of field) and focal length of the camera. A control unit 3 is for controlling the adjustment unit 2 in a sequence set in advance and for instructing the camera 1 to select image capture points on the inspection object 7. An illumination device 4 is for throwing an illumination light to the inspection object 7 substantially from the horizontal direction. A feature quantity extraction unit 15 is for extracting feature quantities of luminance distributions of captured images and a judgement unit 16 is for judging wiring and ball defects such as broken or too close wires and incorrect paths on the basis of the feature quantities.

Figure 3:
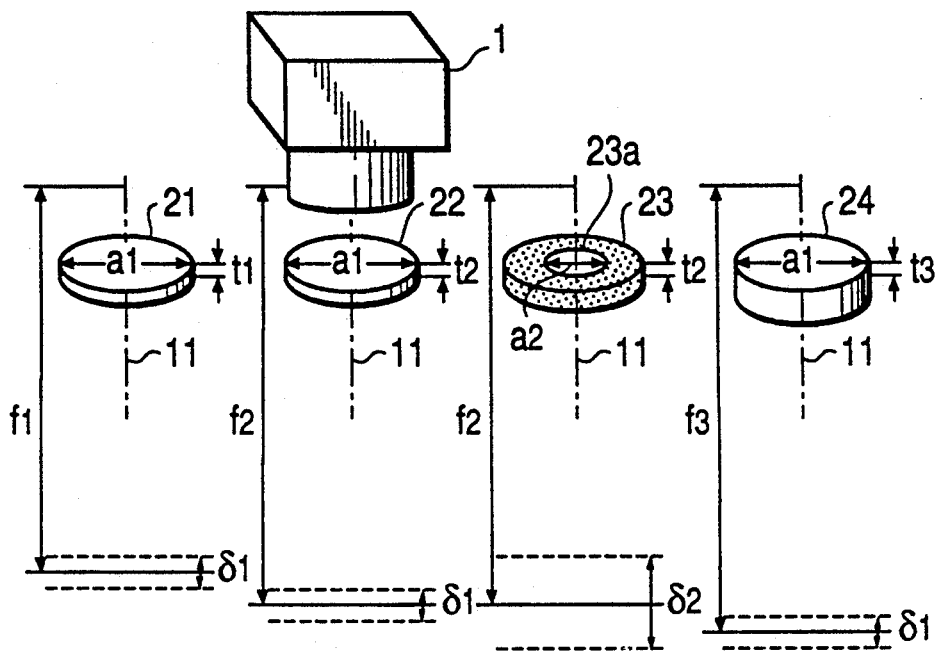
FIG. 3 is an explanatory view showing the structure of glass plates arranged in the bonding wire inspection apparatus.

The adjustment unit 2 comprises a support frame 20 formed of a circular plate rotatably mounted about its center axis for supporting a plurality of glass plates (four glass plates in this embodiment) 21, 22 . . . 24 and a motor 25 for rotating the supporting frame 20 intermittently by a predetermined rotational angle. These first, second, third and fourth glass plates 21, 22 . . . 24 are arranged annularly on the frame 20 and formed of optically dense material having a refractive index, respectively. Each glass plate is designed to have a predetermined thickness and diameter. An anti-reflection coating is applied on the surface of each glass plate. As shown in FIG. 3, the first short glass plate 21 has a thickness $t_1$ and a diameter $a_1$ to allow the camera to have a first focal length $f_1$ focal point is located on a slice level $F_1$ which is determined at a position higher than the top portion of the curved shape of a bonding wire 70 (FIG. 6(A) to (C))) and a first small focal depth $\delta_1$. The second glass plate 22 has a thickness $t_2$ and diameter $a_1$ to allow the camera 1 to have a second intermediate focal length $f_2$ (its focal point is located on a slice level $F_2$ which is determined at an intermediate position of the curved shape of the wire 70) and a first small focal depth $\delta_1$.

The third glass plate 23 as a thickness $t_2$ and a diameter $a_2$ to allow the camera to have the second intermediate focal length $f_2$ and a second large depth of field $\delta_2$. In addition, the fourth glass plate 24 has a thickness $t_3$ and a diameter $a_1$ to allow the camera 1 to have a long focal length $f_3$ (its focal point is located at a slice level $F_3$ which is determined at a position close to the lower portion of a chip 71) and a first small depth of field $\delta_1$. The relationships between the thicknesses $t_1$, $t_2$, $t_3$ and between the focal depths $\delta_1$, $\delta_2$ are $t_3 > t_2 > t_1$ and $\delta_2 > \delta_1$, respectively. The glass plate 23 is covered with a stopper screen 23a to decrease an opening portion.

In general, the optical path of an optical element having a thickness t and a refractive index n is determined by the product (t×n) of the thickness t by the refractive index n, and the focal depth of the optical element is determined by the dimension of the diameter thereof acting as a stop. Therefore, if a plurality of glass plates with various diameters and thicknesses are selectively disposed on an optical axis 11 of the above optical system, the focal length and the focal depth of the optical system can be changed.

In this embodiment, the fourth glass plate 24 allows the camera 1 to have the largest focal length f₃ because of its largest thickness t₃, and the third plate 23 allows the camera 1 to have the focal depth δ₂ larger than the focal depth δ₁ of the other three glass plates 21, 22, 24. It is desirable that the focal depth δ₂ should be equal or close to the total height of the semiconductor as an inspection object to find out the existence of the bonding wire 70.

Figure 4:
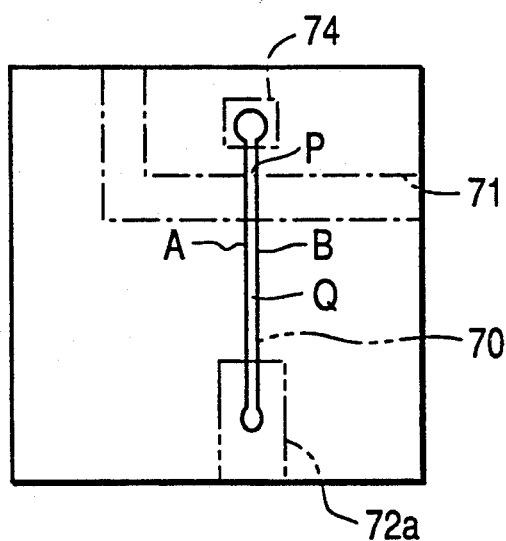
FIG. 4 is a plan view of a bonding wire for explaining extraction of a feature quantity.

The feature quantity extraction unit 15 calculates, as shown in FIG. 4, luminance distributions at a plurality of points P, Q on the bonding wire 70, along a line segment A-B perpendicular to the bonding wire 70 disposed between an inner lead 72a and a pad 74 on a chip 71 (FIG. 6(A) to (C), 22).

The point P is selected at a position corresponding to the top portion of the curved shape of the wire 70, and the point Q is selected at a position corresponding to a portion close to the inner lead 72a.

Figure 5A:
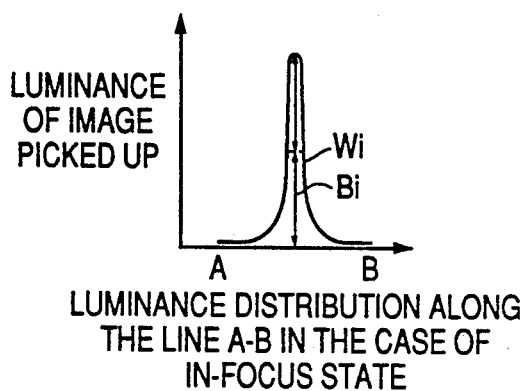
Figure 5B:
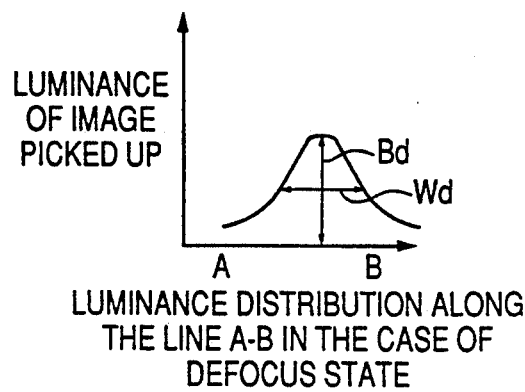
FIG. 5B is a luminance distribution diagram taken along the line A-B in FIG. 4 in the case of an out-of-focus state.

FIG. 5A shows a luminance distribution when an image of the point P or Q is in focus while FIG. 5B shows a luminance distribution when an image of the point P or Q is out of focus. In FIG. 5A, a width $W_i$ of a peak of luminance distribution is small and a height $B_i$ of the peak is large. In FIG. 5B, a width $W_d$ of a peak of luminance distribution is large in comparison with the width $W_i$ thereof and a height $B_d$ of the peak is small in comparison with the height $B_i$ thereof.

The feature quantity extraction unit 15 calculates, at each of the points P, Q, the ratio of the height B of the peak of luminance distribution to the width W of the peak to extract a focal point evaluation quantity E as a feature quantity which is determined by the following equation.

$$E = B/W$$

That is, the focal point evaluation quantity E represents the degree of an in-focus state of an image at the selected points P, Q on the bonding wire 70.

A judgement unit 16 (shown in FIG. 2) makes a comparison between focal point evaluation quantities E at each of captured points P, when the focal length of the camera 1 is determined at three lengths $f_1, f_2, f_3$ thereby to detect wiring and ball defects.

As shown in FIG. 2, the illumination device 4 has an annular illumination unit 5 which is formed with an annular body 6 arranged between the adjustment unit 2 and the inspection object 7. A light source 8 is disposed at a lateral position of the annular body 6 for emitting an illumination light. One ends of a large number of optical fibers 9 are opposed to the light source 8 and the other ends 9b of the optical fibers 9 are arranged downwardly in an annular shape in the body 6. Under the annular body 6 is provided an optical path changing unit 10 which comprises a conical annular mirror in which the inspection object 7 is disposed. The conical annular mirror has an inclined reflecting surface 10a for changing vertical optical path of a light emitted vertically from the lower annularly arranged ends of the optical fibers 9 into a substantially horizontal optical path thereof to irradiate the inspection object 7 therewith in the horizontal direction.

Instead of the conical mirror, an elliptic cone or square cone may be used.

An optical path changing unit 10 is supported movably in the upward and downward directions by a driving unit 211 for moving the optical path changing unit 10 vertically within a predetermined range. The driving unit 211 is composed of a drive cylinder 12 containing an electromagnet therein, a support frame 13 for supporting the driving unit 211, and a support plate 14, fixed to the lower end of a piston rod 12a of the drive cylinder 12, for supporting the optical path changing unit 10 at its front end. The support frame 13 has an upper frame 13a and a lower frame 13b disposed parallel to each other, and the front ends of the two upper and lower frames 13a, 13b are opposed to each other to function as a stopper for restricting the upper and lower limit positions of the optical path changing unit 10.

Instead of the driving unit 211, a cam mechanism may be used.

The operation of this embodiment will now be explained with reference to FIGS. 2, 6(A) to (C) and 7.

Figure 8A:
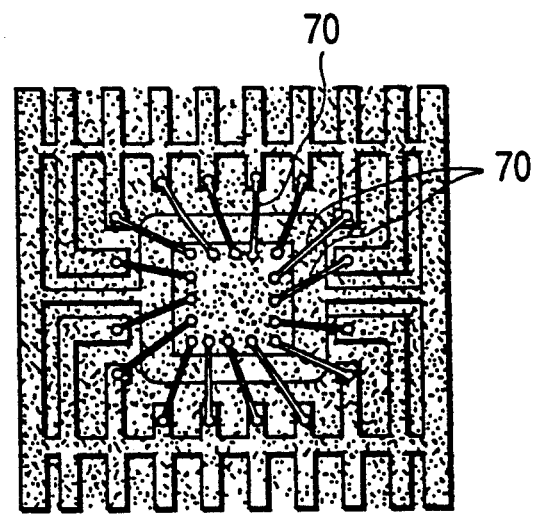

First, the inspection object 7 is carried or conveyed by a frame feeder (not shown) to a predetermined position where the center of the inspection object 7 coincides with the optical axis 11 of the camera 1. At this time, the drive cylinder 12 operates the optical path changing unit 10 to take its upper limit position where the support frame 14 abuts against the front end of the upper frame 13a. Therefore, the optical path changing unit 10 does not obstruct conveyance of the inspection object. After the inspection object 7 is transmitted to the predetermined position, the optical path changing unit 10 is moved downwardly by the operation of the drive cylinder 12 to its lower limit position where the support plate 14 abuts against the front end of the lower support frame 13b. In this state, a light emitted from the light source 8 enters the one ends 9a of the bundle of the optical fibers 9 and travels therethrough to vertically come out of the other ends 9b thereof arranged at the lower end of the annular body 6. A vertical optical path of the light emitted therefrom is changed into a substantially horizontal optical path. Therefore, the inspection object 7 is irradiated, at its entire periphery thereof, with the substantially horizontal light whose light angle is very small with respect to the horizontal direction. By this horizontal illumination, the images of all bonding wires on a semiconductor as the inspection object are brightened in a dark field of view as shown in FIG. 8A.

In this manner, the optical system is ready for inspection of the three dimensional shape or structure of each of the bonding wires 70 on the semiconductor. As shown in FIG. 2, the motor 25 of the adjustment unit 2 is, first, driven to rotate the unit 2 by a predetermined angle so that the center axis of the glass plate 23 coincides with the optical axis 11 of the camera 1. Accordingly, the camera is adjusted to have the focal depth δ₂ larger than the focal depth of other glass plates 21, 22, 24 and the second focal length f₂ to capture an image of an intermediate portion (line A-B (FIG. 4)) of the wire 70 (step 1). The image of the wire 70 is picked up or captured by the camera 1 to output a video signal at the maximum depth δ₂ (step 2). Since the focal depth δ₂ of the glass plate 23 is sufficiently large, the existence of the wire 70 can be detected even if the wire 70 has a defect. This video signal is inputted to the control unit 3 to determine slice levels of the inspection object 7 with respect to the focal lengths $f_1, f_2, f_3$, respectively (step 3). Further, the control unit 3 drives the motor 25 to rotate it by predetermined angle thereby to rotate, in order, each of the glass plates 21, 22 and 24 to a position coinciding with the optical axis 11 thereof for adjusting the camera 1 so as to have the determined first to third focal lengths $f_1$, $f_2$, $f_3$, respectively. By this rotation, the camera 1 is adjusted to have the determined first to third focal length $f_1$, $f_2$, $f_3$ and a first focal depth $\delta_1$ smaller than the second focal depth $\delta_2$ to detect the shape of the wire 70 (step 4). At this time, two image capture points P, Q of each bonding wire 70 on the inspection object 7 are selected by means of the control unit 3 with respect to the first to third focal lengths $f_1$, $f_2$, $f_3$. That is, in a state where the first glass plate 21 is located on the optical axis 11 of the camera 1, the image of the position P on each wire 70 is captured to obtain a video signal. The second glass plate 22 is then located on the optical axis thereof to capture the images of the positions P, Q and, thereafter, the fourth glass plate 24 is located on the optical axis thereof to capture the image of the point Q.

Respective video signals provided by image capture in step 5 are inputted to the feature quantity extraction unit 15. This feature quantity extraction unit 15 calculates respective focal point evaluation, quantities $E_{P1}$, $E_{P2}$, $E_{Q2}$ and $E_{Q3}$ on the basis of respective video signals to extract the feature quantities (step 6).

The judgement unit 16 judges whether or not, with respect to each of focal point evaluation quantities $E_{P1}$, $E_{P2}$, $E_{Q2}$ and $E_{Q3}$, the reference relationships of $E_{P1} > E_{P2}$ and $E_{Q2} > E_{Q3}$ are satisfied (step 7).

Figure 6A:
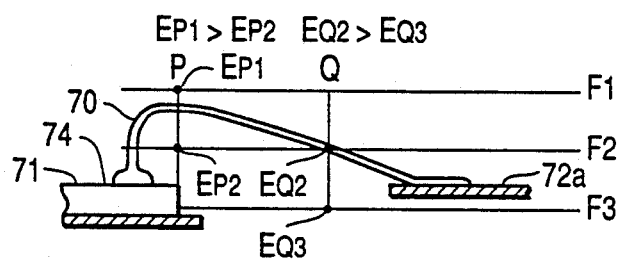
Figure 6B:
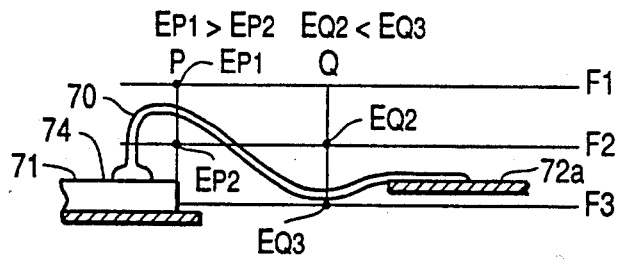
Figure 6C:
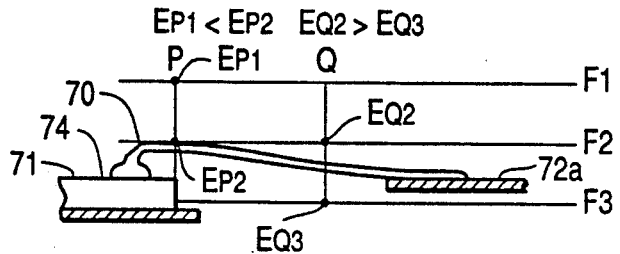
Figure 7:
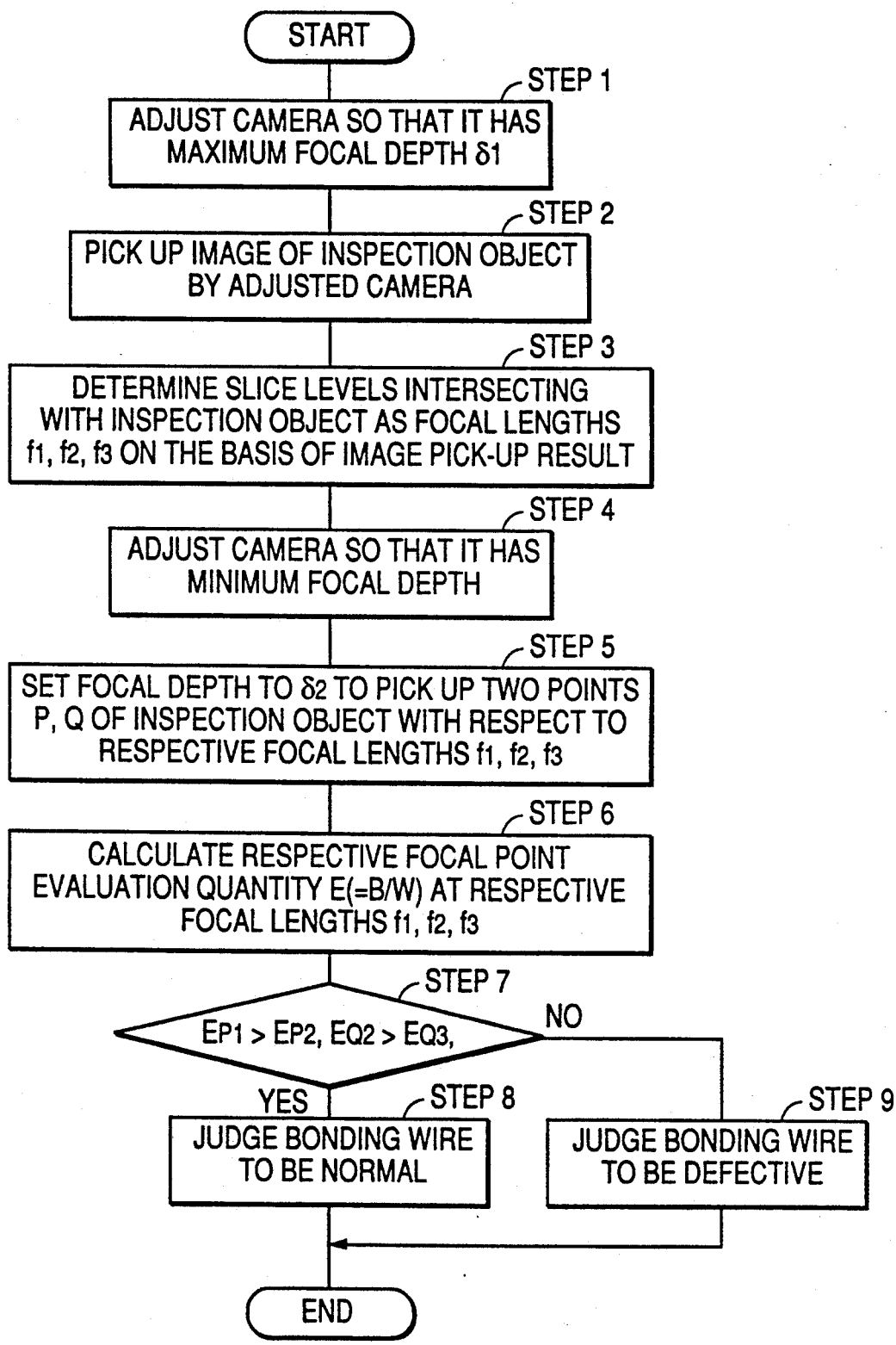
FIG. 7 is an operating flowchart of an embodiment of this invention.

In the case where the respective reference relationships are obtained, the judgement unit 16 judges that the bonding wire is in a normal state as shown in FIG. 6A (step 8). On the other hand, in the case where the respective reference relationships are not obtained, the judgement unit 16 judges that the bonding wire 70 has defects, that is, a wire suspending defect (FIG. 6B) or the wire over-stretching defect (FIG. 6C) (step 9). That is, the relationship $E_{P1} > E_{P2}$ represents that a portion of the wire 70 corresponding to the point P is located, in its height position, at a position nearer the slice level $F_1$ than the slice level $F_2$ as shown in FIGS. 6A and 6B. The relationship $E_{P1} < E_{P2}$ represents that a portion of the wire 70 corresponding to the point P is located, in its height position, at a position nearer the slice level $F_2$ than the slice level $F_1$ as shown in FIG. 6C. Further, the relationship $E_{Q2} > E_{Q3}$ represents that a portion of the wire 70 corresponding to the point Q is located at a position nearer the slice level $F_2$ than the slice level $F_3$ as shown in FIGS. 6A and 6C. On the other hand, the relationship $E_{Q2} < E_{Q3}$ represents that a portion of the wire 70 corresponding to the point Q is located at a position nearer the slice level $F_3$ than the slice level $F_2$ as shown in FIG. 6B.

According to this invention, since the focal length and depth are changed by a plurality of glass plates 21, 22, ... 24, it is not necessary that the positions of the inspection object 7 and the camera 1 are changed to vary the focal length and depth. Therefore, a complicated moving mechanism for precisely moving little by little a support means for supporting the inspection object 7 or the camera 1 is not required. In addition, since the ratio of the luminance distribution is adopted as a feature quantity to detect the shape of the wire 70, even if a certain portion of the wire to be detected is not located at a predetermined focal point, its height position can be generally detected.

Figure 9:
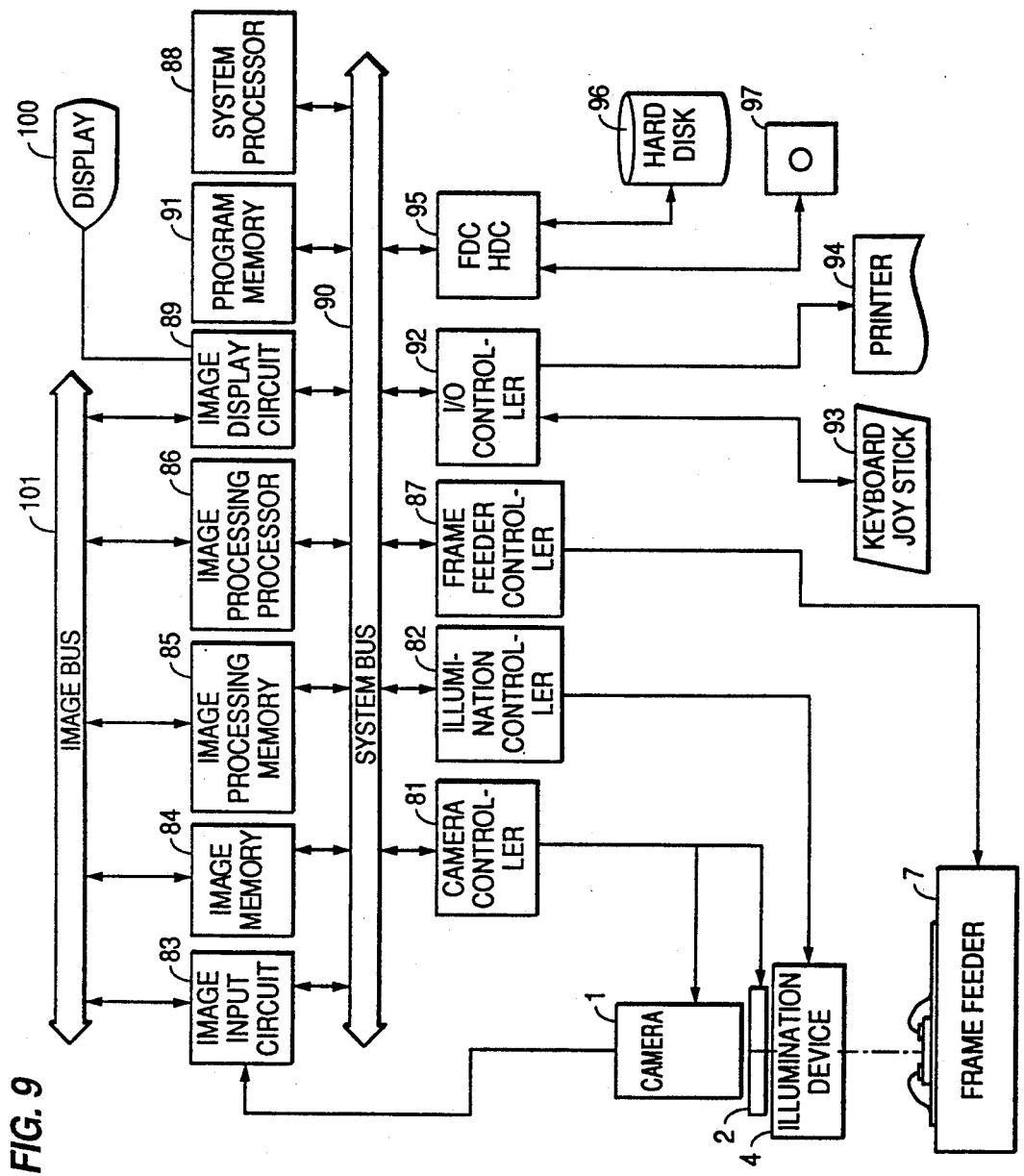
FIG. 9 is a block diagram of an embodiment having a microcomputer of this invention.

This invention may be controlled by a microcomputer which is shown in FIG. 9. That is, the microcomputer has a camera controller 81 for controlling the camera 1 and the glass plates 21, 22 ... 24 of the adjustment unit 2 so as to coincide with the optical path of the camera 1 in order. An illumination controller 82 controls the illumination device 4 to throw an illumination light to the inspection object 7. Further, a frame feeder controller 87 controls the frame feeder so as to allow the inspection object 7 to be carried or conveyed to a position on the optical axis of the camera 1.

A video signal of the inspection object 7 captured on the basis of the control of the camera controller 81 is digitalized by an image input circuit 83. The video signal inputted through the image input circuit 83 is stored into an image memory 84. It is desirable that the number of frames of the image memory 84 should be equal to at least the number corresponding to the number of the glass plates 21 to 24.

An image processor 86 reads out, through an image processing memory 85 as a buffer memory, a video signal stored in the image memory 84 in the case where the glass plate 23 is located on the optical axis thereof. This image processor 86 judges whether or not the bonding wire 70 exists at a predetermined position A-B (see FIG. 4) of the inspection object 7. Since the image of the bonding wire 70 is captured as a bright line, if the bonding wire 70 exists, the above-mentioned judgement can be carried out with ease by the image processor 86. The second optical depth $\delta_2$ is set, at the position corresponding to the second focal length $f_2$, at the range of a sufficient depth including the top portion of the bonding wire 70 and the lower end of the inspection object 7 as mentioned above.

In the case where it is judged by the image processor 86 that the bonding wire 70 exists, a system processor 88 instructs the camera controller 81 to effect a control for switching, in order, the glass plates 21, 22 and 24 of the adjustment unit.

Further, in FIG. 9, an image display circuit 89 is provided between a system bus 90 and a display 100 such as a CRT for displaying an image of the wire 70. The above elements 83, 84, 85, 86, 88, 89 are provided between an image bus 101 and the system bus 90. The microcomputer has also a program memory 91 in which a control program for controlling the optical system are stored, an I/O controller 92 to which a keyboard, joy stick 93 and a printer 94 is connected, and a floppy or hard disk controller (FDC, HDC) 95 for controlling a hard disk 96 and a floppy disk 97.

Figure 10:
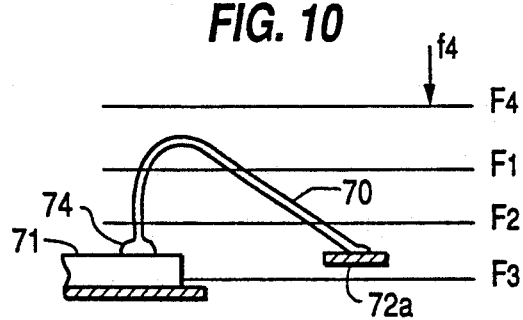
FIG. 10 is a view showing a loosening defect of the bonding wire.

In the above-described embodiment, an arrangement is employed such that adjustment of the adjustment unit 2 is made at two stages with respect to the focal depth (first and second focal depths $\delta_1$ and $\delta_2$), and at three stages with respect to the focal length the first, second and third focal lengths $f_1$, $f_2$ and $f_3$), respectively. In addition, such an arrangement may be employed to adjust the focal length at a plurality of stages more than the respective numbers. If a slice level $F_4$ is set at an upper position over the slice level $F_1$, and a glass plate having a focal length $f_4$ and the first focal depth $\delta_1$ is provided, wire loosening defect as shown in FIG. 10 can be detected.

Figure 11:
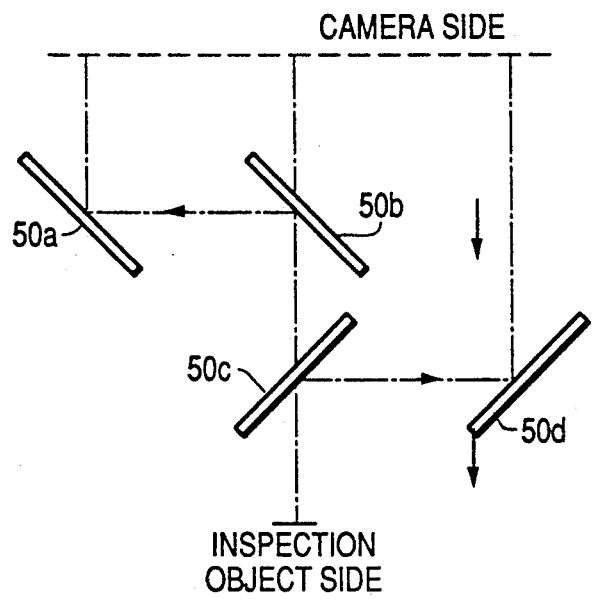
FIG. 11 is a block diagram of an adjustment unit constructed with a plurality of half mirrors.
Figure 12:
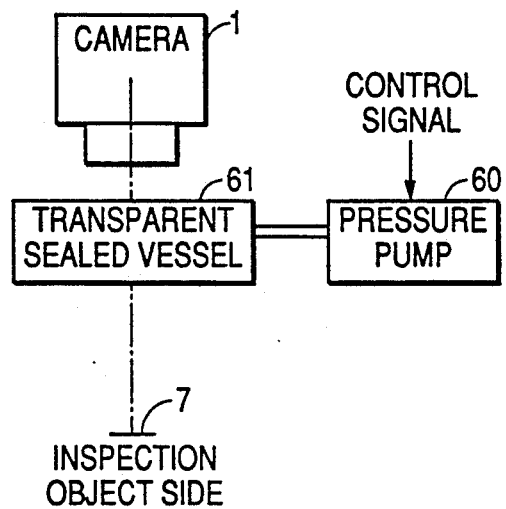
FIG. 12 is a block diagram of an adjustment unit constructed with a transparent sealed vessel.

Further, two arrangements may be employed as shown in FIGS. 11 and 12. FIG. 11 shows an arrangement in which a plurality of half mirrors 50a, 50b, ... 50d are arranged in combination, thus to vary the focal point at a plurality of stages in its height position by changing an optical path by the half mirrors 50a, 50b, ... 50d. Further, FIG. 12 shows an arrangement for adjustment of pressure in which transparent gas or transparent liquid is supplied by pressure pump 60 into a transparent sealed or closed vessel 61 between the camera and the inspection object 7 to arbitrarily the refractive index within the transparent sealed vessel 61.

As an illumination device for irradiating the inspection object 7, the following structure may be also employed. That is, in the above embodiment, a large number of optical fibers are used for emitting a light to the inspection object 7. However, a plurality of spot light emitting bodies such as LED's may be arranged in an annular form instead of the optical fibers.

As mentioned above, the illumination device is provided to irradiate the bonding wires 70 of the inspection object 7 with a horizontal light. However, it is desirable that some other mechanisms should be additionally arranged in order to recognize clearly a pad and the inner lead of a lead frame onto which both ends of each bonding wire are bonded and which are generally flat.

Figure 13:
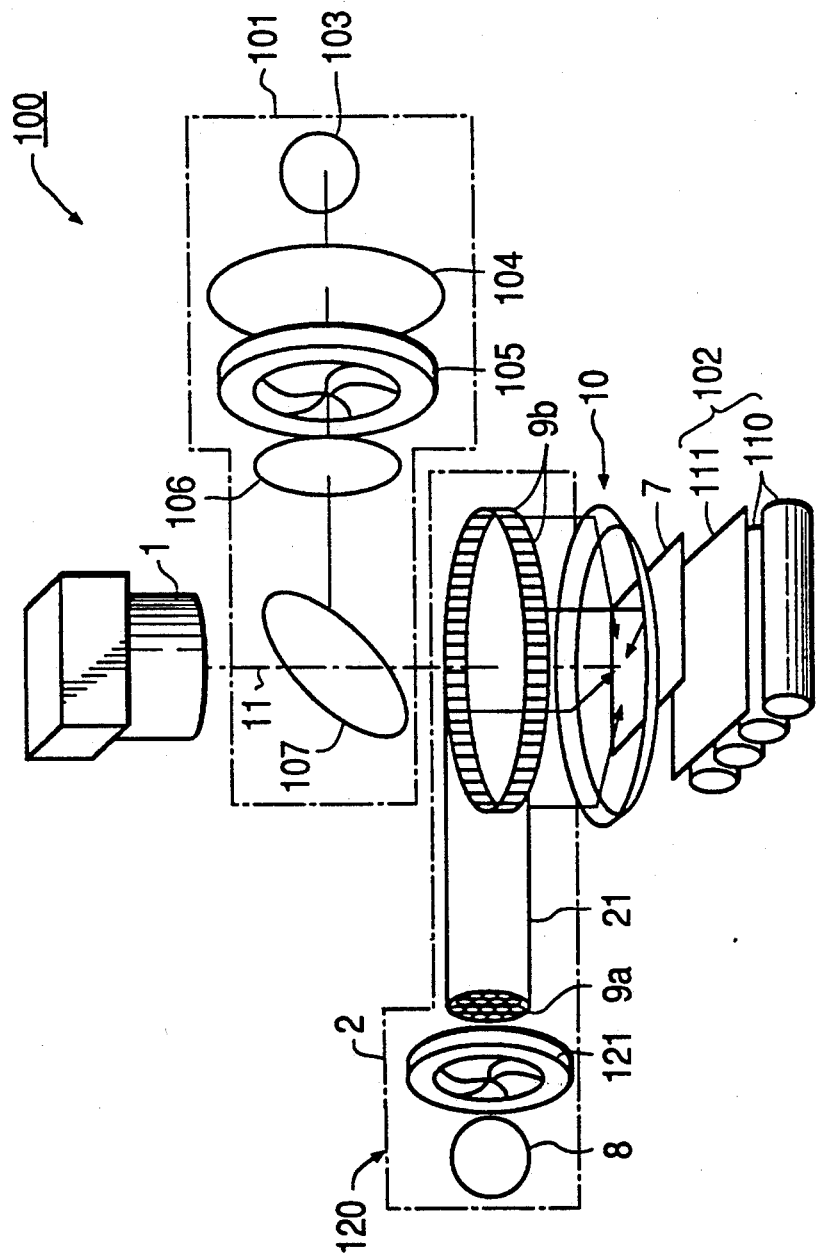
FIG. 13 is a diagrammatic view showing another embodiment of an illumination system.

FIG. 13 shows an illumination device 100 which has a vertical illumination mechanism 101 for throwing vertically an illumination light onto the inspection object 7 just from above, an annular illumination unit 120 for emitting light in an annular manner, an optical path changing unit 10, and a back illumination unit 102 for irradiating the inspection object 7 with an illumination light from back.

The vertical illumination mechanism 101 comprises a light source 103 serving as a light emitting body, a non-spherical lens 104 for changing an illumination light from the light source 103 to parallel illumination light, a shutter 105 provided on the emitting side of the nonpherical lens 104 to control travelling of the illumination light, a diffusing plate 106 provided on the emitting side of the shutter 105 to diffuse the illumination light to provide a homogeneous illumination light, etc., and a half mirror 107 for downwardly directing the illumination light emitted from the diffuse plate 106 in the same direction as that of the optical axis 11 of the camera 1.

The back illumination unit 102 comprises a light source 110 provided under the inspection object 7 and formed with a plurality of columnar light emitting bodies disposed parallel to each other in a horizontal direction, and diffusing plate 111 provided between the light source 110 and the inspection object 7 for diffusing an illumination light emitted from the light source 110 thereby to provide a homogenous illumination light.

The annular illumination unit 120 has a structure similar to that of the annular illumination unit 5 which comprises the light source 8 and a plurality of optical fibers 9 whose one ends 9a are bundled and opposed to the light source 8 and whose other ends are disposed annularly over the inspection object 7. In addition to those members, the annular illumination unit 120 has a shutter 121 between the bundled ends 9a of the optical fibers 9 and the light source 8 for controlling travel of the illumination light from the light source 8.

The operation of this embodiment will now be explained.

When the bonding wire inspection operation mentioned above is performed, the annular illumination unit 120 is operated to irradiate the inspection object 7 with a horizontal illumination light in a state wherein the annular and back illumination units 101, 102 are not operated. That is, the shutter 121 is opened to permit the illumination light from the light source 8 to pass therethrough to be incident onto the bundled ends 9a of the fibers 9. The illumination light thus passing through the optical fibers 9 comes out of the lower ends 9b of the fibers arranged annularly. The illumination light emitted therefrom is directed to the inspection object 7 through the optical path changing unit 10 in the same manner as that in the above-mentioned embodiment shown in FIG. 2. At this time, the image of bonding wires 70, shown in FIG. 8A, is thus obtained.

Figure 8B:
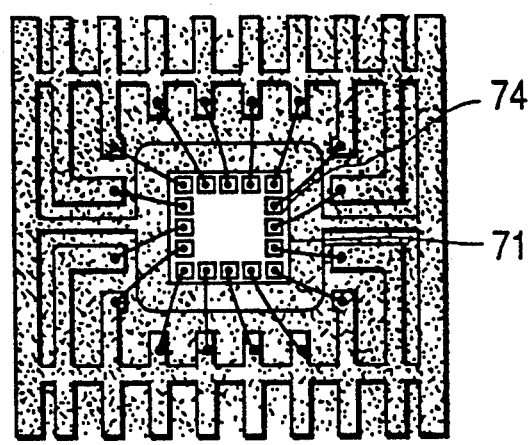
Figure 14:
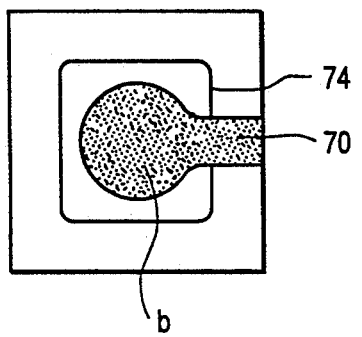
FIG. 14 is an enlarged plan view of an image of a pad when a semiconductor is irradiated by a vertical illumination unit.

After the bonding wire inspection is completed, each pad 74 of the IC chip 71 is inspected with the annular and back illumination units 120, 102 in a non-operated state. The shutter 121 of the annular illumination unit 120 is closed to interrupt an illumination light from the light source 8, while the shutter 105 of the vertical illumination unit 100 is opened to allow an illumination light from the light source 103 to pass therethrough and to be reflected from the half mirror 107 in a direction along the optical axis 11. Thus, the illumination light is downwardly directed to the inspection object 7 just from above. This illuminating state is shown in FIG. 8B. In FIG. 8B, only the flat surface of the IC chip 71 reflects the illumination light upwardly. Thus, it shines. The enlarged plan view of the pad 74 in the IC chip 71 is shown in FIG. 14. In FIG. 14, it is possible to clearly recognize the contour of the pad 74, and the contrast with respect to the bonding ball portion b (dark shadow portion of black) of the bonding wire 70 connected to the center portion of the pad 74 becomes clear. Accordingly, it is possible to inspect whether or not the bonding wire 70 is properly bonded onto the pad 74.

Figure 15:
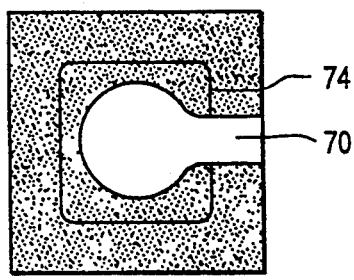
FIG. 15 is an enlarged plan view of an image of the pad when the semiconductor is irradiated by a conventional illumination unit.

In contrast, when the vertical illumination unit 101 is not used, an image of the pad 74 shown in FIG. 15 is obtained.

Figure 8C:
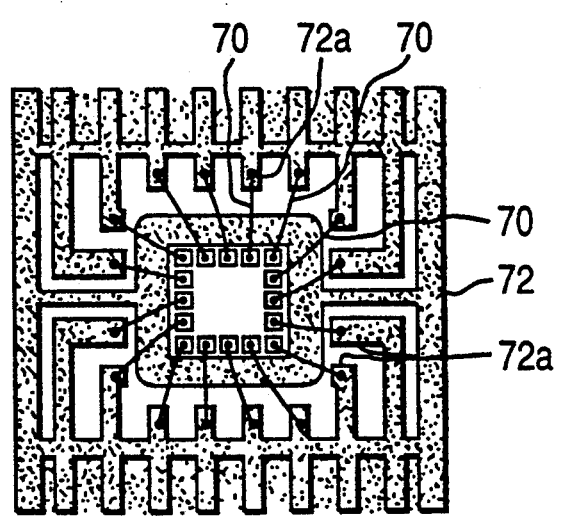

After inspection of the pad 74 in the IC chip 71 is completed, the portion of the inner lead 72a in the lead frame 72 is then inspected. At this time, the shutters 105 and 121 are both closed to irradiate the back side of the inspection object 7 with an illumination light emitted from the back illumination unit 102. This illuminating state is shown in FIG. 8C. In FIG. 8C, the lead frame 72 can be captured as a silhouette image thereof in the inspection object 7. Particularly, it is thus possible to clearly identify the inner lead 72a of the lead frame 72 finely worked, thus to inspect whether or not the bonding wire 70 is properly processed.

It is to be noted that while, in the above-mentioned embodiment, the illumination device 4 comprises both of vertical illumination unit 101 and the back illumination unit 102 in addition to the annular illumination unit 120, an arrangement including only one of the vertical illumination unit 101 and the back illumination unit 102 in addition to the annular illumination unit 120 may be employed. Further, illumination may be conducted by a combination of various illumination units such as polarized illumination unit, etc. in addition to the vertical illumination unit or back illumination unit.

In addition, while an arrangement to switch the annular illumination unit 120, the vertical illumination unit 101 and the back illumination unit 102 to carry out illumination in this order is employed in the above-mentioned embodiment, an arrangement to inspect an arbitrary portion to be illuminated in an arbitrary order may be employed.

Further, in the annular illumination units 4, 120 of the above-mentioned embodiments, optical elements such as optical fibers are arranged annularly over the inspection object 7. However, they may be constructed with an illumination of other forms, such as, ellipse form, or rectangle form, etc.

In the above embodiment, the optical path changing unit 10 formed of an annular reflecting mirror is used for changing the optical path of the illumination light. As the structure of the annular reflecting mirror, the following structure may be adopted to increase a horizontal illumination efficiency.

Figure 16:
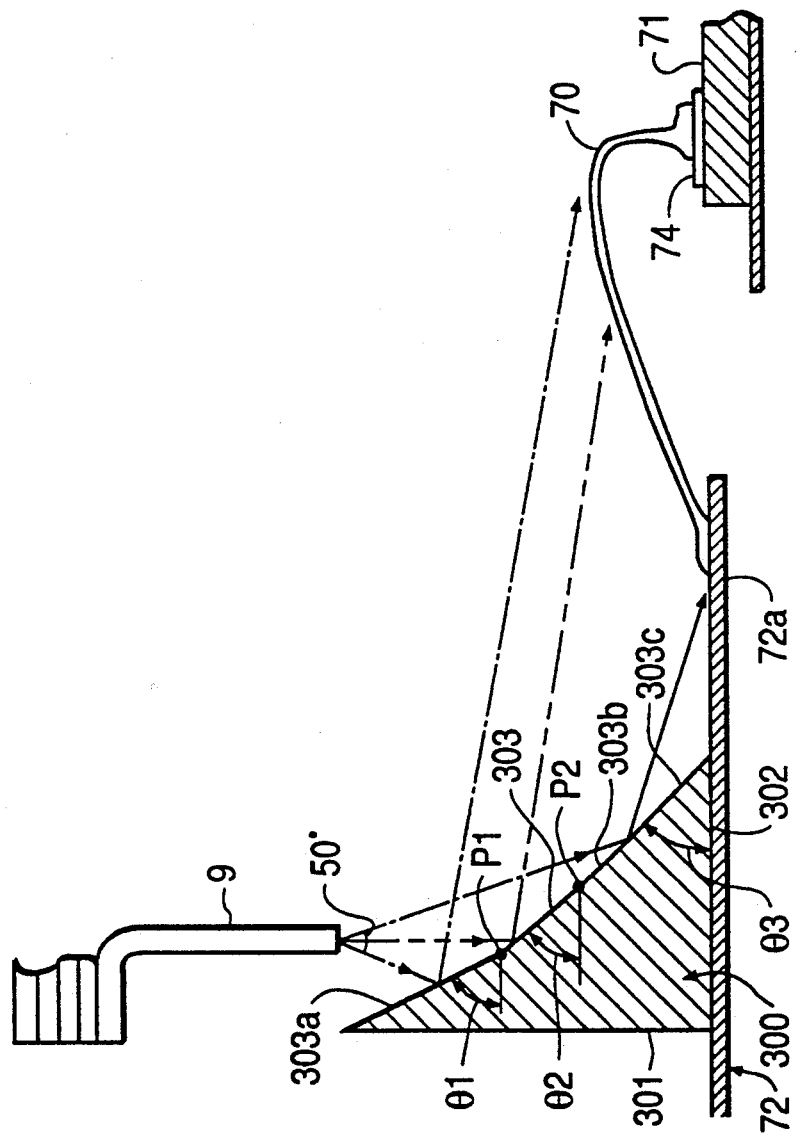
FIG. 16 is a sectional view of an annular mirror as an optical path changing means according to this invention.

In FIG. 16, an annular mirror 300 has a back surface 301, a bottom surface 302 placed on the lead frame 72 and an inclined reflecting surface 303 for directing a vertical light coming out of the lower end 9b of the optical fiber 9 to the bonding wire 70. The inclined reflecting surface 303 is bent at two intermediate points $P_1$, $P_2$ in its longitudinal section and comprises an upper linear surface 303a, an intermediate linear surface 303b and a lower linear surface 303c. With respect to the lead frame 72, for example, the upper, intermediate and lower linear surfaces 303a, 303b and 303c have three inclination angles $\theta_1$, $\theta_2$, $\theta_3$ of 75, 60 and 45 degrees, respectively.

A light emitted from the optical fiber 9 diverges about 50 degrees. The diverged light is reflected at the three divided linear surfaces 303a, 303b, 303c to be effectively condensed within the height of the bonding wire 70. In general, an upper portion of the bonding wire 70 is irradiated with an illumination light at an incident angle which is larger than an incident angle at which an illumination light is incident on a lower portion thereof. Therefore, the image of the upper portion thereof is apt to be darker than that of the lower portion thereof. In view of this defect, the three inclined angles $\theta_1$, $\theta_2$, $\theta_3$ are selected to increase condensing level of light at the upper portion thereof thereby to obtain a uniform brightness of an image through the entire height of the bonding wire 70. This improvement of the annular reflecting mirror increases the illumination efficiency to two times in comparison with a conventional annular mirror 304, shown in FIG. 17, having a linear inclined reflecting surface 305 without any bent portion as shown in FIG. 17.

Figure 18:
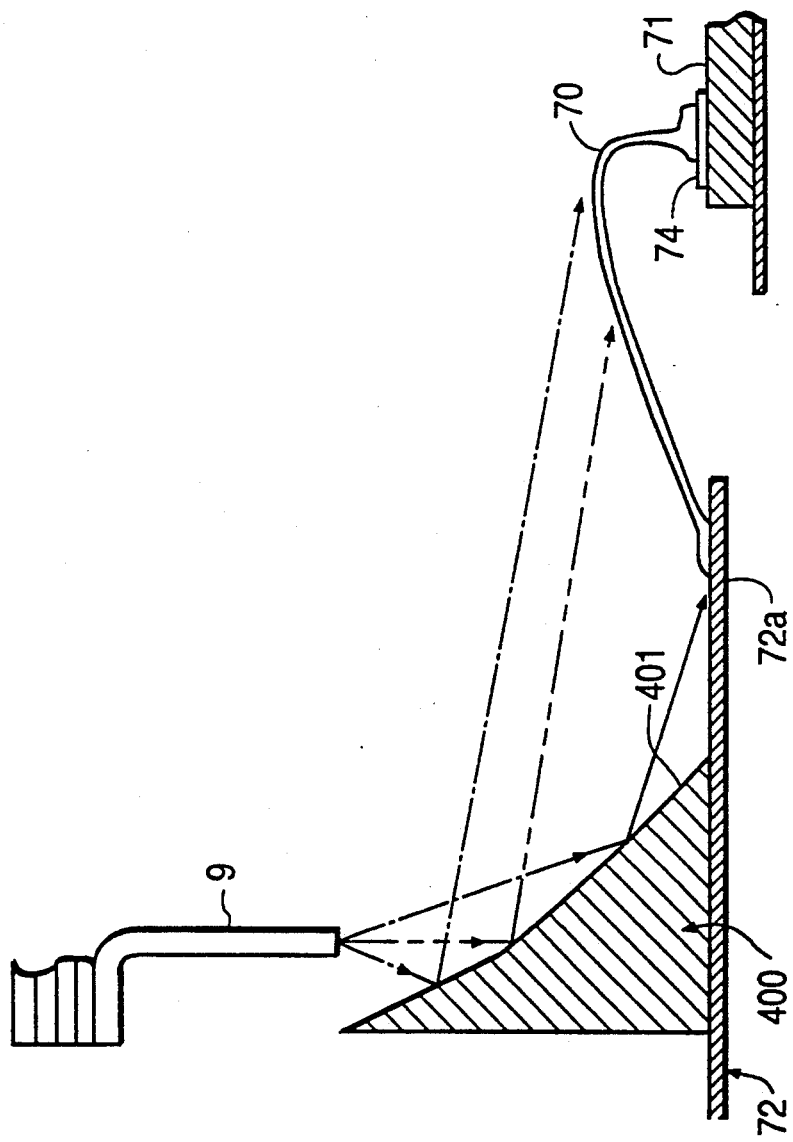
FIG. 18 is a sectional view of an annular mirror showing another embodiment of the optical path changing unit.

Instead of the annular mirror 300 having the bent inclined surface 303, an annular mirror 400 having a smoothly curved surface 401 may be used (FIG. 18).

Figure 19:
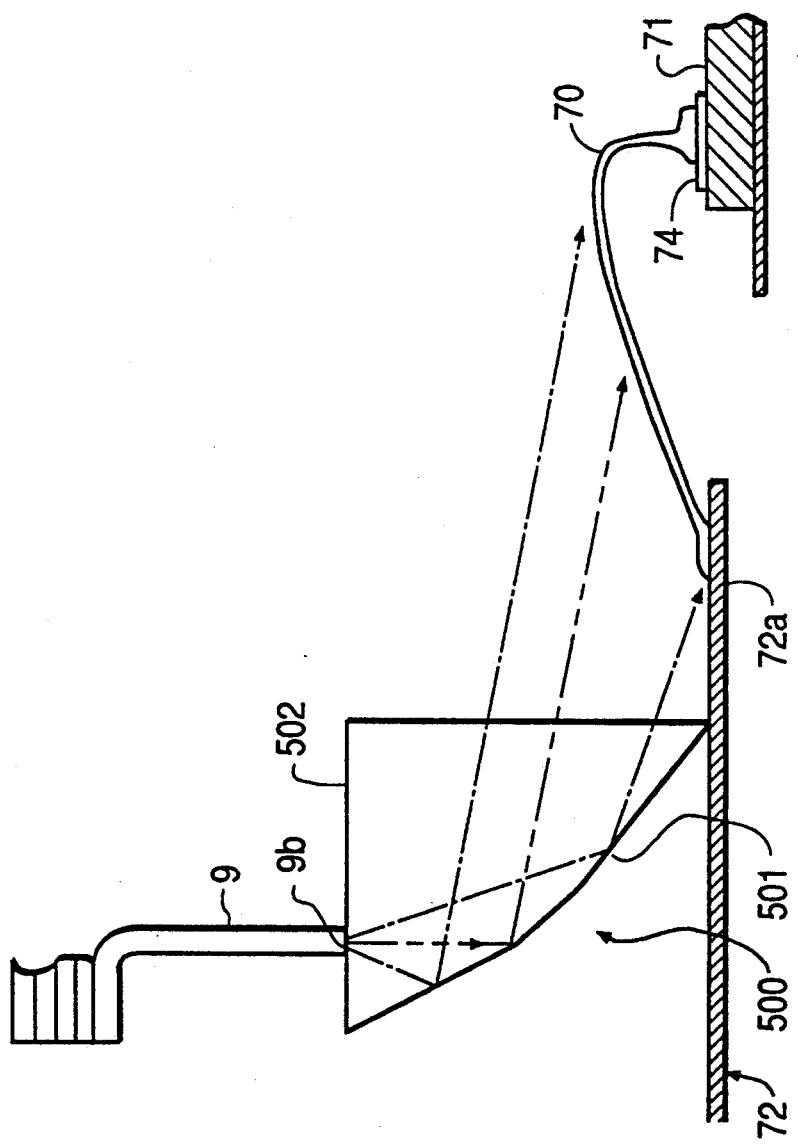
FIG. 19 is a sectional view of an annular mirror showing still another embodiment of the optical path changing unit.

Further, instead of the annular mirrors 300, 400, an annular prism 500 having an outer curved surface 501 may be arranged (FIG. 19). In this case, the lower end 9b of the fiber 9 contacts the upper horizontal surface 502 thereof.

Figure 17:
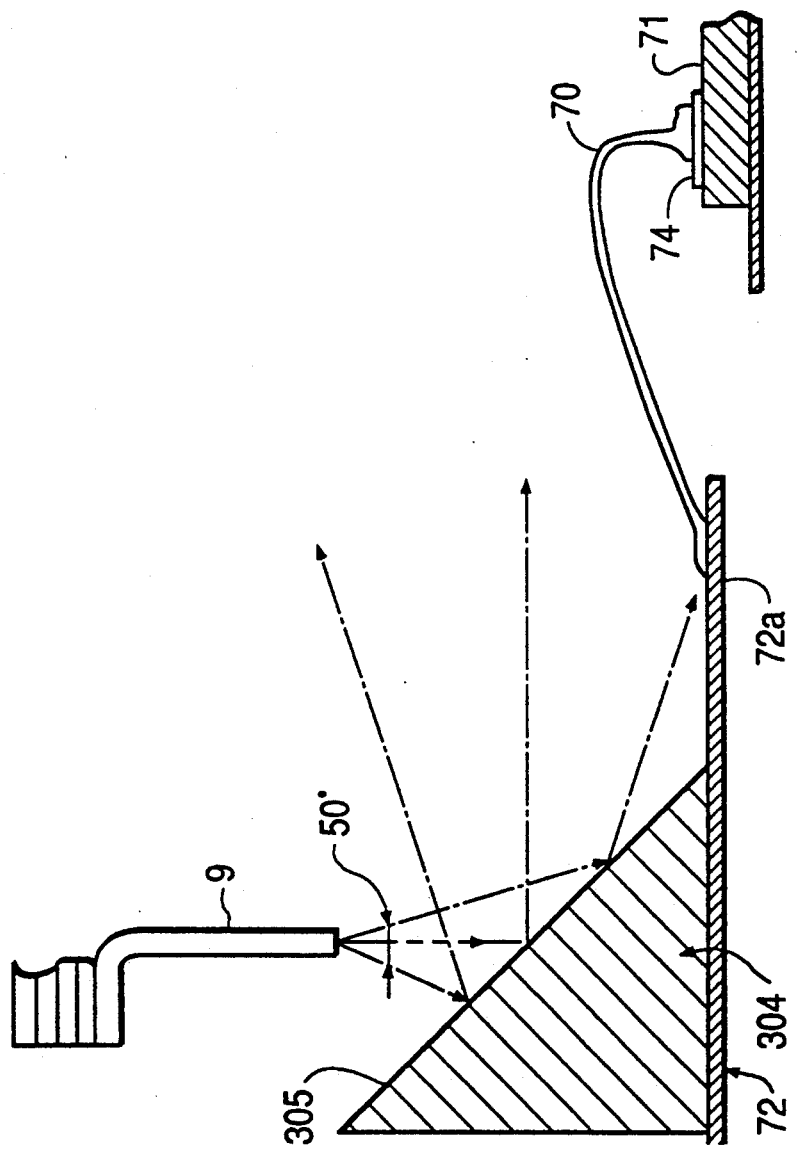
FIG. 17 is a sectional view of a conventional annular mirror.
Figure 20:
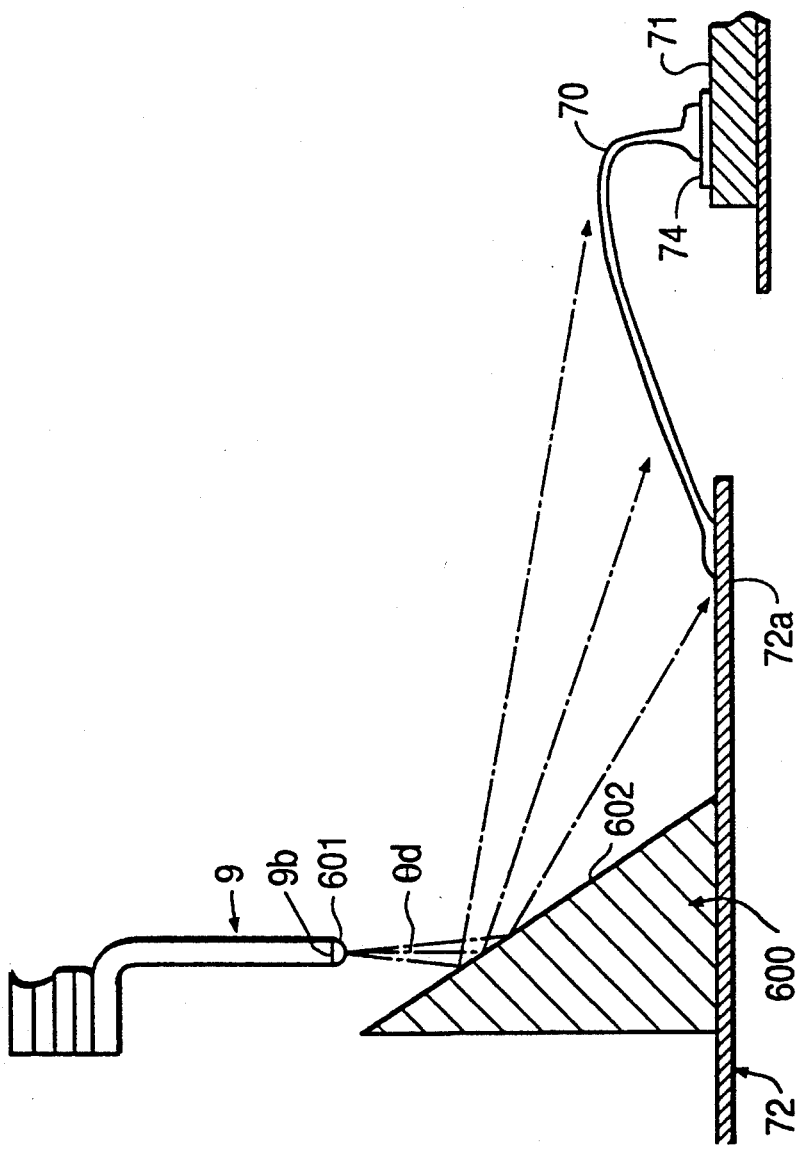
FIG. 20 is a sectional view of an annular mirror showing still another embodiment of the optical path changing unit.

In the case that a conventional type of annular mirror 600 having a straightly inclined surface 602 is used as shown in FIG. 20, convex lens 601 may be formed at the lower end face of the optical fiber 9 to decrease a diverging angle $\theta d$ of a light coming out thereof and a straightly inclined surface 602 whose inclined angle is larger than that of the typical inclined surface shown in FIG. 17. This structure is simpler than those of the above improved annular mirrors.

The above camera 1 as an image capture means may be a typical ITV camera. However, a typical CCD camera has 500×500 pixels. The diameter of a bonding wire is about 20 μm and its length is 2 to 3 mm. In addition, the range where all bonding wires are bonded is about 20 mm×20 mm. Accordingly, if image capture is performed with a resolution sufficient to capture an image of the bonding wire, the entire range of all the bonding wires cannot be captured. If image capture is performed over the entire range of all bonding wires, its resolution becomes insufficient, failing to correctly detect defects.

Figure 21:
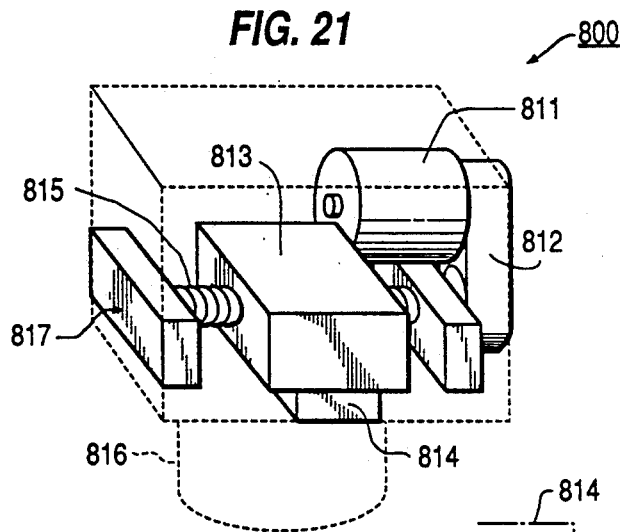
FIG. 21 is a schematic view of a camera as an image capture means.

In order to solve this problem, a camera 800 shown in FIG. 21 may be used. That is, the camera 800 is composed of a CCD line sensor 814 serving as a one-dimensional solid-state image capture element, and a uniaxial movement stage 817 for moving the CCD line sensor 814 over the inspection object 7 for scanning it. The stage 817 comprises a sensor holding table 813 for holding the CCD line sensor 814, and a ball screw 815 engaged with the sensor holding table 813. The camera 800 has an image forming lens 816 at its lower end. The ball screw 815 is rotated by a motor 11 through a timing belt 812.

The operation of this embodiment will now be described.

Figure 22:
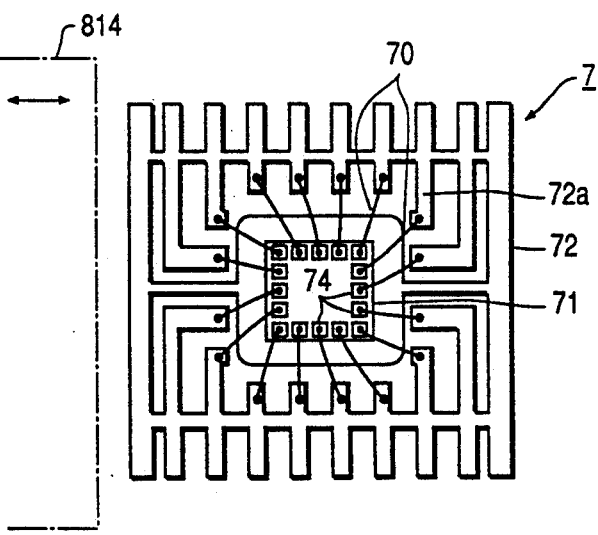
FIG. 22 is a plan view of an inspection object.

A bonding wire is generally made of gold or aluminum having a diameter of about 30 μm. Each bonding wire 70 is, as shown in FIG. 22, bonded between the pad 74 on the IC chip 71 and an inner lead 72a, the length of the bonding wire is 2 to 3 mm, and the bonding range is about 20 mm×20 mm. Accordingly, from a viewpoint of a diameter of the bonding wire 70, it is required that the resolution is about 5 μm. Further, from a viewpoint of the bonding range, about 4000 elements are required for the CCD line sensor 814. Since the element size of the CCD line sensor 814 having about 4000 elements is 7 μm, the optical magnification of the image forming lens 816 is set at 1.4. The camera 800 captures images corresponding to one line every time the sensor holding table 813 moves by a feed pitch of 7 μm. By repeating this operation 4000 times while moving the table 813 at a constant speed, the image of the bonding range of 20 mm×20 mm of the inspection object 7 can be correctly captured with a resolution of 5 μm. Accordingly, it is possible to inspect precisely wiring on the inspection object 7.

Further, while the number of elements constituting the CCD line sensor 14 is about 4000, a CCD line sensor having the other number of elements such as 5000 may be employed. In addition, the optical resolution of the image forming lens 816 may be changed.

What is claimed is:

1. A method of inspecting bonding wires as an inspection object on a semiconductor in which a camera captures images of the inspection object while irradiating the inspection object with an illumination light to obtain a video signal which is to be processed to detect defects, said method comprising the steps of:

(a) providing a plurality of light-permeable plates for selective use with the camera, each light-permeable plate having an aperture size with a corresponding focal depth and a thickness with a corresponding focal position;

(b) capturing an image of at least one selected portion of the inspection object with one of the light-permeable plates to obtain image information including an amount of defocus of the first image of the inspection object and a height of the at least one selected portion of the inspection object based on a luminance distribution of the at least one selected portion;

(c) repeating step (b) a predetermined number of times, using different light-permeable plates providing different focal positions and focal depths each time; and (d) making a comparison between the information for the at least one selected portion at the different focal positions of the inspection object to detect defects.

2. A method according to claim 1, wherein said providing in step (a) provides at least four light-permeable plates with different combinations of focal depth and focal position including a first combination of a first short focal position and a first small focal depth, a second combination of a second intermediate focal position and the first small focal depth, a third combination of a third intermediate focal position and a second large focal depth, and a fourth combination of a third long focal position and the first small focal depth.

3. A method according to claim 1, wherein said repeating in step (c) includes the substep of selecting two portions of the inspection object to capture images, where one portion is near a top portion of the inspection object and the other portion is near an intermediate portion of the inspection object, and at least three levels being set with respect to a height position of the inspection object, a first level being set at a position over the top portion of the inspection object, a second level being set at an intermediate height position thereof, a third level being set at a lower portion of the inspection object, and the light-permeable plates being selected so that three focal positions coincide with the three levels, respectively.

4. A method according to claim 2, wherein said capturing in step (b) is repeated by step (c) to perform the substeps of:

(b1) capturing a first image of the inspection object using one of the light-permeable plates with the third combination of the second intermediate focal position corresponding to an intermediate height position of the inspection object and the second large focal depth including a top portion of the inspection object and a lower portion of the inspection object to detect existence of the inspection object, and (c2) capturing second and third images of the top and lower portions, respectively, using other of the light-permeable plates having different focal positions and the first small focal depth.

5. A method according to claim 1, wherein step (e) includes the substep of:

(e1) capturing the feature quantities which are each a ratio of a height of a peak of the luminance distribution to a width of the peak.

6. An apparatus for inspecting a bonding wire as an inspection object on a semiconductor in which a camera captures an image of the inspection object while irradiating the inspection object with an illumination light to obtain a video signal which is to be processed to detect defects, said apparatus comprising:

a plurality of light-permeable plates, each having a thickness with a corresponding focal position and an aperture size with a corresponding focal depth;

focal position and depth adjusting means for adjusting focal position and depth of the camera by selecting at least one of said plurality of light-permeable plates;

feature information extraction means for extracting feature information including an amount of defocus of an image of at least one selected portion of the inspection object and a height of the at least one selected portion based on a luminance distribution at the at least one selected portion; and judgement means for comparing the feature information at different height positions of the selected portion of the inspection object to detect defects.

7. An apparatus according to claim 6, wherein said focal position and depth adjusting means comprises a frame which rotates about a center axis of said frame, said plurality of glass plates being arranged annularly around said frame, each of said plurality of light-permeable plates being movable so that an axis of each of said plurality of light-permeable plates coincides with an optical axis of the camera.

8. An apparatus according to claim 7, wherein said plurality of light-permeable plates comprises:

a first light-permeable plate with a first short focal position and a first small focal depth, a second light-permeable plate with a second intermediate focal position and the first small focal depth, a third light-permeable plate with the second intermediate focal position and a second large focal depth, and a fourth light-permeable plate with a third long focal position and the first small focal depth.

9. An apparatus according to claim 6, further comprising:

illumination means for irradiating the inspection object with the illumination light, and including:

an annular illumination means for emitting the illumination light in an annular shape, optical path changing means for directing the illumination light to the inspection object located in said optical path changing means, and driving means for moving vertically said optical path changing means.

10. An apparatus according to claim 9, wherein said driving means comprises a stopper for stopping said optical path changing means at upper and lower limit positions.

11. An apparatus according to claim 6, further comprising:

illumination means for irradiating the inspection object with the illumination light, including:

annular illumination means for emitting the illumination light in an annular shape, and optical path changing means for directing the illumination light to the inspection object located in said optical path changing means, said optical path changing means comprising an annular reflecting mirror having an inner inclined reflecting surface comprising a plurality of linear surfaces each having a different inclination angle for condensing the illumination light to an upper portion of the inspection object more than a lower portion of the inspection object.

12. An apparatus according to claim 6, further comprising:

illumination means for irradiating the inspection object with the illumination light, including:

annular illumination means for emitting the illumination light in an annular shape, and optical path changing means for directing the illumination light to the inspection object located in said optical path changing means, said optical path changing means comprising an annular reflecting mirror having an inner reflecting smoothly curved surface for condensing the illumination light to an upper portion of the inspection object more than a lower portion of the inspection object.

13. An apparatus according to claim 6, further comprising:

illumination means for irradiating the inspection object with the illumination light, including:
    annular illumination means for emitting the illumination light in an annular shape, and
    optical path changing means for directing the illumination light to the inspection object located in said optical path changing means, said optical path changing means comprising an annular reflecting prism having a reflecting surface for condensing the illumination light to an upper portion of the inspection object more than a lower portion of the inspection object.

14. An apparatus according to claim 6, further comprising:
    illumination means for irradiating the inspection object with the illumination light, and includes:
    annular illumination means for emitting the illumination light in an annular shape, and
    optical path changing means for directing the illumination light to the inspection object located in said optical path changing means,
    and wherein said annular illumination means comprises a number of glass fibers which are arranged annularly and whose light emitting ends are formed so as to decrease a diverging angle,
    and wherein said optical path changing means comprises an annular reflecting mirror having an inner inclined linear surface.

15. An apparatus according to claim 6, further comprising:
    illumination means for irradiating the inspection object with the illumination light and includes:
    a light source means for providing the illumination light;
    annular illumination means for emitting the illumination light in an annular shape,
    optical path changing means for directing the illumination light to the inspection object located in said optical path changing means, for directing the illumination light the inspection object located in said optical path changing means, and
    vertical illumination means for shining the illumination light onto the inspection object from above and
    back illumination means for irradiating a back surface of the inspection object with the illumination light, each of said vertical and back illumination means including a shutter for controlling travel of the illumination light emitted from said light source means.

16. An apparatus according to claim 6, wherein the camera comprises line sensor means for scanning over the inspection object.

17. An apparatus for inspecting an inspection object on a semiconductor in which a camera captures an image of the inspection object while irradiating the inspection object with an illumination light to obtain a video signal which is to be processed to detect defects, said apparatus comprising:
    illumination means for irradiating the inspection object with the illumination light;
    annular illumination means for emitting the illumination light in an annular shape;
    optical path changing means for directing the illumination light to at least one selected portion of the inspection object located in said optical path changing means, said optical path changing means comprising a conical annular mirror for reflecting the illumination light in a substantially horizontal direction on to the inspection object; and
    driving means for moving vertically said optical path changing means.

18. An apparatus according to claim 17, wherein said driving means comprises a stopper for stopping said optical path changing means at upper and lower limit positions.

19. An apparatus according to claim 17, the camera comprises a line sensor for scanning over the inspection object.

20. An apparatus for inspecting an inspection object on a semiconductor in which a camera captures an image of the inspection object while irradiating the inspection object with an illumination light to obtain a video signal which is to be processed to detect defects, said apparatus comprising:
    illumination means for irradiating the inspection object with the illumination light;
    annular illumination means for emitting the illumination light in an annular shape;
    optical path changing means for directing the illumination light to at least one selected portion of the inspection object located in said optical path changing means,
    said optical path changing means comprising an annular reflecting mirror having an inner inclined reflecting surface comprising a plurality of linear surfaces each having a different inclination angle for condensing the illumination light to an upper portion of the inspection object more than a lower portion of the inspection object; and
    driving means for moving vertically said optical path changing means.

21. An apparatus for inspecting an inspection object on a semiconductor in which a camera captures an image of the inspection object while irradiating the inspection object with an illumination light to obtain a video signal which is to be processed to detect defects, said apparatus comprising:
    illumination means for irradiating the inspection object with the illumination light;
    annular illumination means for emitting the illumination light in an annular shape;
    optical path changing means for directing the illumination light to at least one selected portion of the inspection object located in said optical path changing means,
    said optical path changing means comprising an annular reflecting mirror having an inner reflection smoothly curved surface for condensing the illumination light to an upper portion of the inspection object more than a lower portion of the inspection object; and
    driving means for moving vertically said optical path changing means.

22. An apparatus for inspecting an inspection object on a semiconductor in which a camera captures an image of the inspection object while irradiating the inspection object with an illumination light to obtain a video signal which is to be processed to detect defects, said apparatus comprising:
    illumination means for irradiating the inspection object with the illumination light;
    annular illumination means for emitting the illumination light in an annular shape;
    optical path changing means for directing the illumination light to at least one selected portion of the inspection object located in said optical path changing means, said optical path changing means comprising an annular reflecting prism having a reflecting surface for condensing the illumination light to an upper portion of the inspection object more than a lower portion of the inspection object; and driving means for moving vertically said optical path changing means.

23. An apparatus for inspecting an inspection object on a semiconductor in which a camera captures an image of the inspection object while irradiating the inspection object with an illumination light to obtain a video signal which is to be processed to detect defects, said apparatus comprising:

illumination means for irradiating the inspection object with the illumination light;

annular illumination means for emitting the illumination light in an annular shape;

optical path changing means for directing the illumination light to at least one selected portion of the inspection object located in said optical path changing means, said annular illumination means comprising a number of glass fibers which are arranged annularly and whose light emitting ends are formed so as to decrease a diverging angle, and wherein said optical path changing means comprises an annular reflecting mirror having an inner inclined linear surface; and driving means for moving vertically said optical path changing means.

24. An apparatus for inspecting an inspection object on a semiconductor in which a camera captures an image of the inspection object while irradiating the inspection object with an illumination light to obtain a video signal which is to be processed to detect defects, said apparatus comprising:

illumination means for irradiating the inspection object with the illumination light;

annular illumination means for emitting the illumination light in an annular shape;

optical path changing means for directing the illumination light to at least one selected portion of the inspection object located in said optical path changing means;

driving means for moving vertically said optical path changing means;

a light source means for providing the illumination light;

vertical illumination means for shining the illumination light onto the inspection object from above; and back illumination means for irradiating a back surface of the inspection object with the illumination light, each of said vertical and annular illumination means having a shutter for controlling travel of the illumination light emitted from said light source means.

25. A method for inspecting a bonding wire as an inspection object, comprising the steps of:

a) adjusting a focal depth of a plurality of focal depths and a focal position of a plurality of focal positions of a plurality of light-permeable plates, each having an aperture size with a corresponding focal depth and a thickness with a corresponding focal position, of a camera;

b) capturing an image of at least one selected portion of the inspection object based on the one of the focal depths, the one of the focal positions and a luminance distribution of the inspection object;

c) determining feature information including an amount of defocus of the image of the inspection object and a height of the at least one selected portion of the inspection object from the image;

d) repeating steps (a)-(c) to obtain a plurality of feature information; and e) comparing the feature information to detect defects.

26. An apparatus for inspecting a semiconductor device, comprising:

a plurality of light-permeable plates each having an aperture size with a corresponding focal depth and a thickness with a corresponding focal position;

camera means for selecting one of the focal depths and one of the focal positions of said plurality of light-permeable plates, for selecting at least one portion of a wire as an inspection object on the semiconductor device and for imaging the portion of the inspection object at the one of the focal depths and the one of the focal positions; and evaluating means for extracting feature information including an amount of defocus of the image of the inspection object and a height of the at least one selected portion of the inspection object from the imaging and for determining defects from the feature information.

27. An apparatus according to claim 26, wherein said camera means includes a frame, said plurality of light-permeable plates being arranged annularly in said frame.

28. An apparatus according to claim 26, further comprising:

illumination means for illuminating the semiconductor device; and optical means for directing the illumination of the semiconductor device in a specific orientation.

29. An apparatus for inspecting a bonding wire as an inspection object on a semiconductor device, comprising:

a camera to image at least one selected portion of the inspection object at a plurality of focal depths and a plurality of focal positions of a plurality of light-permeable plates, each having an aperture size with a corresponding focal depth and a thickness with a corresponding focal position;

adjustment means for focusing said camera by moving to one of the focal depths and one of the focal positions;

control means for selecting the one of the focal positions moved by said adjustment means and for selecting the at least one selected portion of the inspection object imaged by said camera;

illumination means for shining a light on the semiconductor device;

feature information extraction means for receiving images of the inspection object from said camera and for extracting feature information including an amount of defocus of the images of the inspection object and a height of the at least one selected portion of the inspection object based on a luminance distribution from the images; and judgment means for determining defects from the features information.

* * * * *

UNITED STATES PATENT AND TRADEMARK OFFICE
CERTIFICATE OF CORRECTION

PATENT NO. : 5,298,989
DATED : March 29, 1994
INVENTOR(S) : HIROYUKI TSUKARA et al.

It is certified that error appears in the above-indentified patent and that said Letters Patent is hereby corrected as shown below:

Column 1, line 16, delete "element" and substitute --elements--;

line 50, after "at" insert --a--.

Column 2, line 3, delete "out";

line 16, after "feature" insert --quantity on the basis of luminance distribution at said--;

line 45, after "invention" insert --,--.

Column 4, line 8, change "three dimensional" to --three-dimensional--;

line 10, after "unit" insert --2-- and after "camera" insert --1--;

line 42, delete "Fig." and substitute --Figs.--;

line 49, delete "as" and substitute --has--.

UNITED STATES PATENT AND TRADEMARK OFFICE
CERTIFICATE OF CORRECTION

PATENT NO. : 5,298,989
DATED : March 29, 1994
INVENTOR(S) : HIROYUKI TSUKARA et al.

It is certified that error appears in the above-indentified patent and that said Letters Patent is hereby corrected as shown below:

Column 5, line 47, delete "the" and substitute --an--;

line 52, delete "One ends" and substitute --Ends 9a--.

*Column 6, line 48, change "three dimensional" to --three-dimensional--;

line 54, after "camera" insert --1--.

Column 7, line 22, delete "," after "evaluation".

Column 8, line 45, delete "is" and substitute --are--;

Column 9, line 1, after "by" insert --1-- and after "arbitrarily" insert --vary--;

line 43, after "and" insert --a--.

Column 10, line 56, delete "," after "while".

line 52, after "length" insert --(--.

UNITED STATES PATENT AND TRADEMARK OFFICE
CERTIFICATE OF CORRECTION

PATENT NO. : 5,298,989
DATED : March 29, 1994
INVENTOR(S) : Hiroyuki Tsukara, et. al.

It is certified that error appears in the above-indentified patent and that said Letters Patent is hereby corrected as shown below:

Column 16, line 50, delete "reflection" and substitute --reflecting--.

Signed and Sealed this

Ninth Day of August, 1994

Attest:

BRUCE LEHMAN

Attesting Officer

Commissioner of Patents and Trademarks